Figure 1:
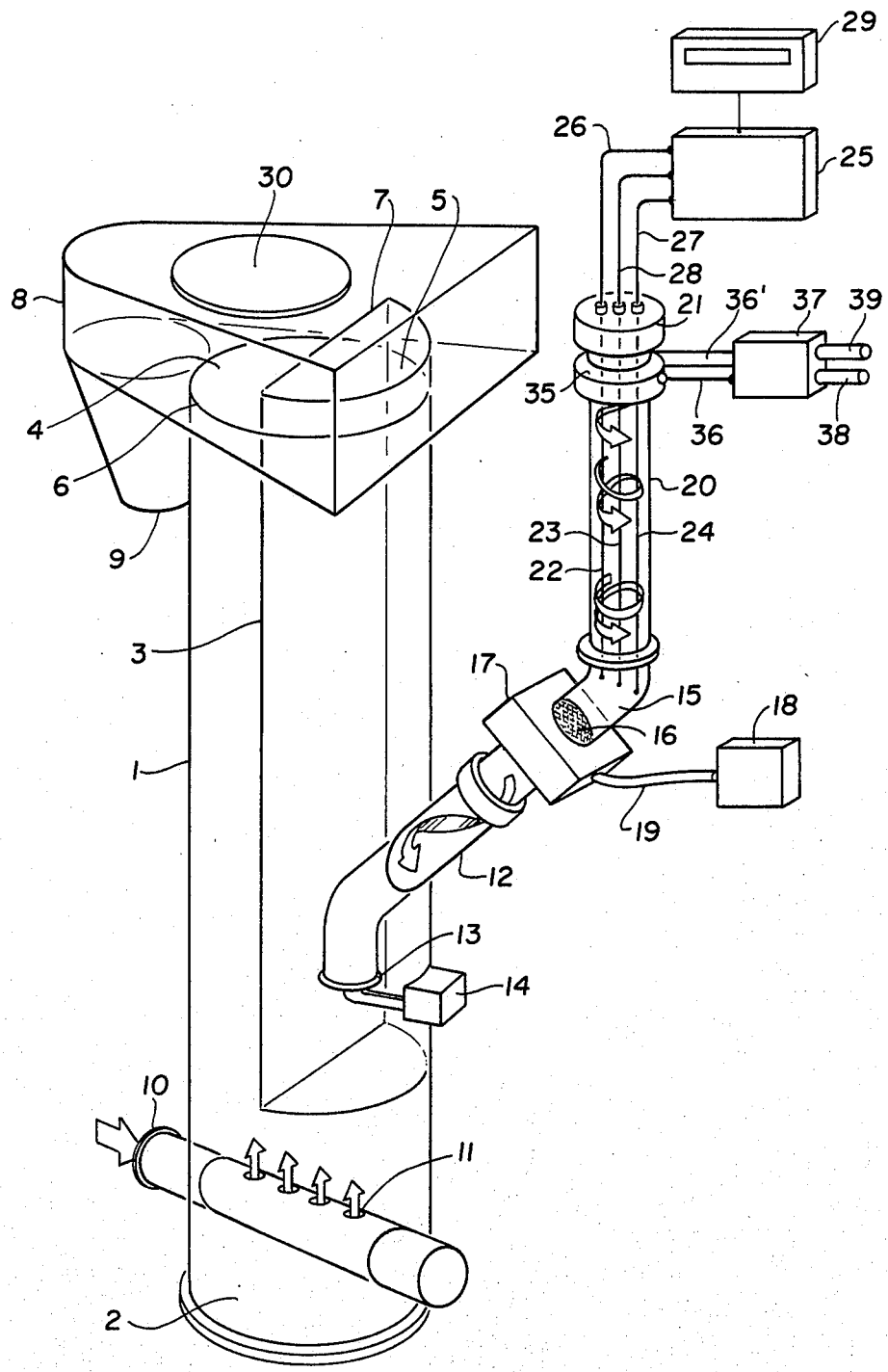

United States Patent [19]

Eriksson

[11] 4,285,231
[45] Aug. 25, 1981

[54] APPARATUS FOR MEASURING THE PARTICLE SIZE RANGE IN A SUSPENSION

[76] Inventor: Kjell R. A. Eriksson, Strandvagen 3, S-542 00 Mariestad, Sweden

[21] Appl. No.: 112,426

[22] Filed: Jan. 16, 1980

[30] Foreign Application Priority Data

Nov. 27, 1979 [SE] Sweden .................................. 7909782

[51] Int. Cl.³ ............................................ G01N 15/00
[52] U.S. Cl. ........................................................ 73/63
[58] Field of Search ................... 73/63, 61 R, 432 PS; 162/198, 263

[56] References Cited

U.S. PATENT DOCUMENTS

| | | | |
|---|---|---|---|
| 3,186,215 | 6/1965 | Danforth | 73/63 |
| 3,330,151 | 7/1967 | Reinhall | 73/63 |
| 3,538,749 | 11/1970 | Danforth | 73/63 |
| 3,688,563 | 9/1972 | Enarsson et al. | 73/63 |
| 3,846,231 | 11/1974 | Crosby et al. | 73/63 X |
| 4,053,354 | 10/1977 | Kitsnik | 73/63 X |
| 4,089,210 | 5/1978 | Tischenko et al. | 73/63 |

Primary Examiner—Gerald Goldberg
Assistant Examiner—Joseph W. Roskos
Attorney, Agent, or Firm—Burgess, Ryan and Wayne

[57] ABSTRACT

The particle size range of a paper pulp suspension is determined by flowing the suspension up a measuring tube having a filter at the bottom thereof. When a plug of suspended material has formed, the inlet of the measuring tube is closed off. A liquid is then fed to a member which forms a gap in the plug of material and passes up through a measured portion of the suspension. The time taken for the liquid to pass through the plug to a given height is indicative of the mean particle size of the suspension.

9 Claims, 3 Drawing Figures

APPARATUS FOR MEASURING THE PARTICLE SIZE RANGE IN A SUSPENSION

The present invention relates to apparatus for measuring the particle size range in a suspension. The suspension which most readily comes to mind is paper pulp which is normally manufactured in one place and then supplied to a paper manufacturer. The paper pulp contains cellulose fibers which may be obtained either through a sulphite process or through a sulphate process. The cellulose fibers are then whole. Cellulose fibers or parts thereof can be produced by a milling process. In the latter case the fibers may be of different sizes and may also form groups together. When a paper pulp containing fibers or fiber fragments is manufactured mechanically it is essential to know the size range of the cellulose particles so that when the supplier receives the paper pulp he is well aware that, when manufacturing paper, he will obtain the correct quality in the paper produced. In order to determine the size range of mechanically produced cellulose particles in a suspension, i.e. in the present case in a paper pulp, the paper pulp is allowed to pass through a vertical through-flow tube, the upper end of which consitutes a spillway. In the through-flow passage, a tube is placed which is also provided at its upper end with a spillway, but located higher than the spillway for the through-flow passage. A stationary column of paper pulp is thus formed in the tube. To the latter tube, between its ends, is connected one end of a measuring tube which becomes vertical towards the other end. Between the ends of the tube is a filter which allows the suspension liquid, i.e. the paper pulp liquid to pass through. The liquid passing through the filter rises into the vertical part of the measuring tube which contains two indicators located at different levels. The two indicators determine the rate of drainage in the suspension which is retarded in front of the filter. If the particles in the suspension are small, it will take longer for the suspension liquid to penetrate through the filter than if the particles in the suspension are larger.

A plug is formed of the suspension particles in front of the filter described above. In reality, therefore, what is measured is the rate of drainage of said plug. However, it is desirable to be able to measure the drainage rate of a plug which is more similar to the layer of paper pulp on a wire cloth.

The present invention aims at fulfilling this object by placing a separating member in front of said filter which cuts off said plug so that a layer is obtained in front of the filter and so that the end of the layer facing the filter is opposite a passage or gap which can receive liquid which may only pass through the separated layer and the filter. The liquid in this case has a predetermined pressure which may be set by suitable means and is between 0.1 and 1.0 bar. The layer corresponds to a layer on a wire cloth.

The actual separating of the layer is performed by means of the same liquid jet which is used for through-flow through the layer.

To ensure that the liquid intended to flow through the layer will only flow therethrough, the inlet end of the measuring tube must be sealed.

The part of the measuring tube connected to the inlet end of the filter is so inclined, according to the invention, that the suspension can only be retained in this part if it is subjected to pressure.

With the inclination of the measuring tube on the inlet side of the filter, it is advantageous according to the invention to have a vertical through-flow passage which is divided into two parts by an inner wall, one part having a spillway which is on a lower level than that of the other part. A stationary suspension will thus accumulate in the other part and the inlet part of the measuring tube is connected to this part.

Three indicators are arranged at three different levels in the vertical part of the measuring tube and these supply information to a calculating device connected to an indicator.

The filter and separating member can be adjusted to different positions, i.e. to positions between a vertical position and a horizontal position and therebetween. The adjustment can be performed by means of a setting member or by placing them in different positions. Another method is to have an intermediate unit in the measuring tube, which is exchangeable, each unit containing a filter with the desired inclination.

Further characteristics of the present invention are clear from the following description.

Figure 2:
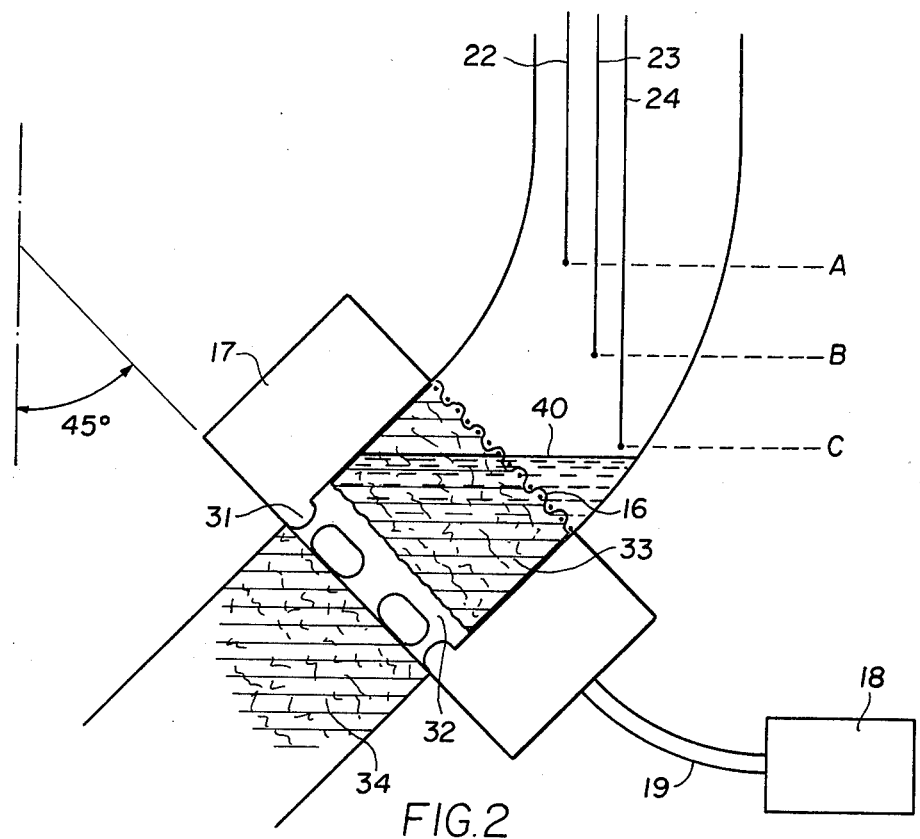
Figure 3:
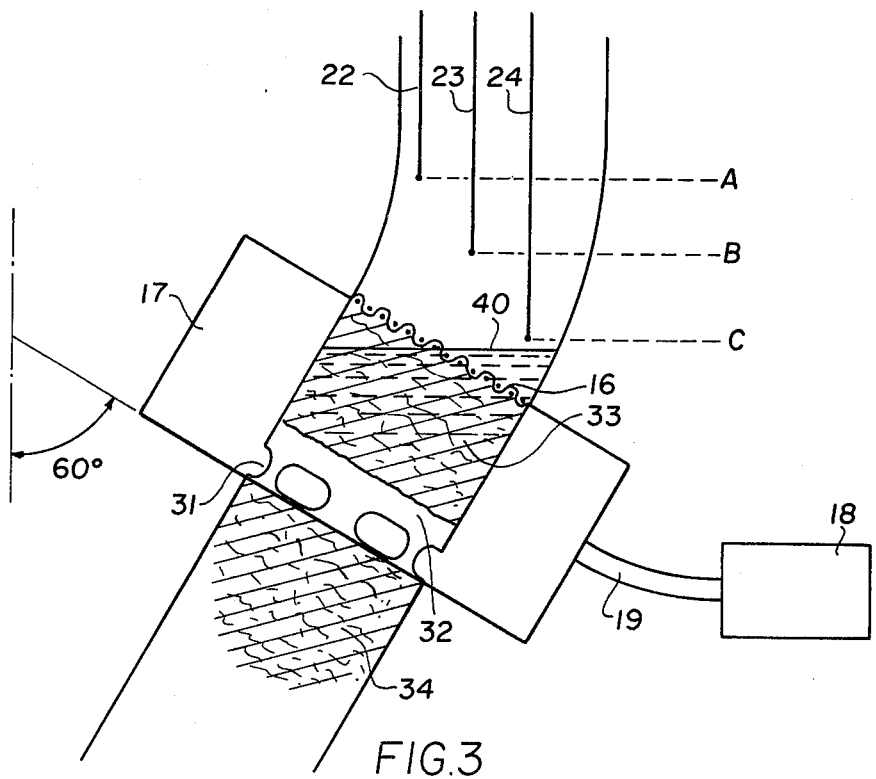

The present invention will be further described with reference to the accompanying two sheets of the drawings in which FIG. 1, partially schematically shows an apparatus according to the present invention and FIGS. 2 and 3, partially schematically show the separating member with filter, enlarged and in two different positions.

In the drawings, 1 is a vertical through-flow passage, preferably in the form of a tube provided with a bottom closure 2. A partition or separating wall 3 is arranged in the tube, which does not reach to the bottom of the through-flow passage but which protrudes outside the lefthand upper edge of the passage 1. The righthand upper edge of the passage is located at the same level as the upper edge of the partition. A lefthand space 4 and a righthand space 5 are thus formed. Both spaces are in the form of a tube, the edge of the lefthand space forming a spillway 6 and the upper edge of the righthand space, which are connected, forming a spillway 7. The openings 4 and 5 of the two spaces open into a collecting vessel 8 with outlet 9. The collecting vessel 8 has an inspection hole 30. At the bottom of the through-flow passage 1, below the inlet opening of the space 5, is an inlet tube 10 passing transversely through the vertical passage. This tube 10 is closed at its righthand end and is provided with a number of outflow openings 11. A measuring tube 12 protrudes into the space 5 and has such inclination that liquid cannot be retained in the tube. The lefthand end of the tube is so directed that its opening surface is perpendicular to the axis of the through-flow passage. In front of the opening is a valve 13 which, with the aid of the control member 14, can either close or open the lefthand end of the measuring tube 12. To the righthand part of the measuring tube 12 is screwed an exchangeable unit 15 containing a filter 16 which forms a certain angle to the vertical plane. The filter 16 is such that it allows through only liquid but not suspended particles. Below the filter 16 is a unit 17 which has the task of cutting off a layer 33 of suspension particles collected in front of the filter 16. The layer 33 of known dimensions is cut off with the help of liquid from a liquid supplier 18 through a conduit 19. The liquid supplier 18 can be set so that the liquid emitted has the desired pressure of between 0.1 and 1.0 bar. The liquid is supplied to the separating member 17 which is provided with a space surrounding the layer formed, and one or more openings 31 which guide the liquid jets so that a gap 32 is formed. On the lefthand side of the gap 32 the remaining suspension 34 is collected. The described unit 15 comprising filter 16 and separating member 17 can be replaced by other units in which the angle of inclination of the filter is different. It is also feasible to arrange a mechanism which can adjust the filter 16 with its separating member 17 to the desired angle in the existing unit.

A vertical extension tube 20, sealed at the upper end with a plug 21, is screwed into the unit 15. Said plug contains three electrodes 22, 23 and 24, the lower ends of which reach the levels A, B and C. The electrodes 22, 23 and 24 are connected to an evaluation means 25 by wires 26, 27 and 28. The evaluation means 25 is connected to an indicator 29. The electrodes 22 and 23 measure the flow time between levels A and B and electrodes 23 and 24 measure the flow time between levels B and C, which is stored in the respective memories. Data from the two memories is processed and stored in a third memory. All the memories are to be found in the means 25. The device is calibrated to correlate flow time with mean particle size in the suspension, and the information obtained in the indicator 29 can be used to alter the size range of the particles in the suspension.

The extension tube 20 is provided at its upper end with a valve unit 35 which, via a wire 36, is connected to a switching unit 37. This unit 37 can either connect the valve 35 with a compressed air unit 39 or with a conduit 38 in communication with the surrounding atmosphere and thus ensures that the ambient atmospheric pressure can be supplied to the valve unit.

The apparatus described above functions as follows: It is assumed that a suspension such as in the present case, paper pulp, prior to delivery is allowed to pass continuously through the vertical through-flow passage 1, through the space 4, to flow over the spillway 6 into the collecting vessel 8 and then leave the vessel 8 through the outlet 9 for delivery. While the paper pulp is flowing up through the space 4 it will also flow up in the space 5. Since the spillway 7 is located on a higher level than the spillway 6, a stationary pillar of paper pulp will be formed in the space 5. The paper pulp flowing in the space 5 also flows up in the measuring tube 12 through its lefthand end when the valve 13 is open. When so much paper pulp has flowed up through the measuring tube 12 that a plug consisting of the parts 33 and 34 has been formed by the suspended material, the lefthand end of the measuring tube 12 is closed by means of the valve 13. In this situation, it is possible that a certain amount of liquid may have flowed through the filter 16. If so, the levels A, B and C are above the liquid level for the liquid 40 which has passed through the filter 16.

When the lefthand end of the measuring tube 12 is closed, liquid is supplied to the cutting member 17 at the desired pressure from the liquid supplier 18. The liquid is allowed to pass through openings 31 so that a gap 32 is formed. When the gap has been formed, the liquid can be supplied at the same pressure or some other desired pressure to the cutting member 17, the liquid supplied being forced to pass through the upper plug or layer 33. The three electrodes 22, 23, and 24 will then measure the times when the liquid from the liquid supplier 18 reaches the various levels A, B and C. The indications from the electrodes 22, 23 and 24 are processed in the evaluation means 25 as described in the following. The result of the evaluation performed in the evaluation means 25 is supplied to the indicator 29.

When the evaluation means 25 has obtained its three indications, the aim is to prepare the measuring tube 12 for the next measurement. For this purpose, the valve 13 is opened. Compressed air is then supplied from the conduit 39 to the valve unit 35 via the conduit 36' and switching member 37. The valve unit 35 was previously supplied with air at atmospheric pressure via the conduit 38. The valve 35 is so designed that air is introduced to the extension tube 20 so that it moves helically along the inner surface of the tube in order to clean the extension tube 20 and to press liquid out of the extension tube as well as pressing liquid and suspension out of the measuring tube 12. Compressed air and liquid will thus flow out of the lefthand end of the measuring tube 12 and the space 5 will thus be emptied of its contents via the spillway 7 so that it can again be filled from below with fresh paper pulp and another measurement can be performed.

It should be obvious that the measuring tube 12 may be provided at the top with a valve unit 35 if desired, to facilitate cleaning.

It should also be obvious that the arrangement with varying angles of the filter 16 is not only limited to the apparatus described. The same applies to the three electrodes 22, 23 and 24 and the separating member 17. Neither is the design and arrangement of the measuring tube 12 limited to the apparatus described.

The division of the through-flow passage 1 as in the present apparatus may also have its uses in other types of apparatus.

The great advantage with three electrodes is that with different paper pulp concentrations it is possible to determine whether the particle size range is the same or different.

What is claimed is:

1. Apparatus for measuring the particle size range in a suspension, comprising a vertical through-flow passage for the suspension, said passage including a space in which a stationary quantity of suspension from the through-flow passage can collect; a measuring tube connected to said space and being provided with a filter which allows liquid through and traps a plug of suspension particles, and a sealing member to cover and uncover the end of said measuring tube at the end by said space; means in said measuring tube to separate a suspension layer of predetermined thickness from said plug in front of the filter thereby producing a gap in front of the layer to permit the passage of liquid under predetermined pressure through the layer and the filter; and means for measuring the flow rate of said liquid through said layer.

2. Apparatus according to claim 1, wherein the filter and the separating means are disposed in the measuring tube in either a vertical or a horizontal position or any position therebetween.

3. Apparatus according to claim 2, wherein the position of the filter and the separating member is adjustable by adjustment means.

4. Apparatus according to claim 1, wherein a liquid supplier is arranged to supply liquid under predetermined pressure to the separating member, said liquid being used both for separating and for passage through said layer.

5. Apparatus according to claim 1, wherein the measuring tube between the filter and its end at said space is so inclined that the measuring tube can only contain suspension if this is subjected to pressure directed against the filter.

6. Apparatus according to claim 5, wherein said end of said measuring tube by the space is provided with an inflow opening, the surface of which is perpendicular to axis of the through-flow passage.

7. Apparatus according to claim 5, wherein said space is formed by a separating or dividing wall in the through-flow passage.

8. Apparatus according to claim 1, 2, 3, 4, 5, 6 or 7, wherein said measuring means comprises three electrodes to measure liquid penetrating through the filter at different levels as a function of time, the liquid flow rate being an indication of mean particle size in said suspension.

9. Apparatus according to claim 8, wherein the measuring tube is connected at the end located on the same side of the filter as the measuring means to a member supplying cleaning medium to the measuring tube so that this is cleaned and ready to receive a fresh quantity of suspension.

* * * * *